(12) United States Patent
Kalsi

(10) Patent No.: US 6,474,706 B1
(45) Date of Patent: Nov. 5, 2002

(54) VEHICLE DOOR LATCH MECHANISM

(75) Inventor: Gurbinder Singh Kalsi, Warley (GB)

(73) Assignee: Meritor Light Vehicle Systems (UK) Ltd., Birmingham (GB)

( * ) Notice: Subject to any disclaimer, the term of this patent is extended or adjusted under 35 U.S.C. 154(b) by 0 days.

(21) Appl. No.: 09/581,355

(22) PCT Filed: Dec. 9, 1998

(86) PCT No.: PCT/GB98/03678

§ 371 (c)(1),
(2), (4) Date: Aug. 7, 2000

(87) PCT Pub. No.: WO99/31341

PCT Pub. Date: Jun. 24, 1999

(30) Foreign Application Priority Data

Dec. 12, 1997 (GB) .............................................. 9726215

(51) Int. Cl.7 ................................................. E05C 3/06
(52) U.S. Cl. ................. 292/216; 292/201; 292/DIG. 23
(58) Field of Search ................................ 292/201, 216, 292/DIG. 23, DIG. 25

(56) References Cited

U.S. PATENT DOCUMENTS 6,148,657 A * 11/2000 Roncin ..................... 292/201 X
6,199,923 B1 * 3/2001 Rice et al. .................. 292/216
6,254,148 B1 * 7/2001 Cetnar ......................... 292/201
6,386,599 B1 * 5/2002 Chevalier .................... 292/201

FOREIGN PATENT DOCUMENTS

| DE | 19619824 | 11/1997 |
| EP | 331832 | 9/1989 |
| EP | 775793 | 5/1997 |
| EP | 806533 | 11/1997 |
| GB | 2106983 | 4/1983 |
| GB | 2220976 | 1/1990 |
| GB | 2278699 | 12/1994 |
| GB | 2307506 | 5/1997 |
| GB | 2313150 | 11/1997 |

* cited by examiner

Primary Examiner—Teri Pham Luu
(74) Attorney, Agent, or Firm—Wood, Phillips, Katz, Clark & Mortimer

(57) ABSTRACT

Vehicle door latch mechanism with child safety facility includes a base plate 12 having a throat 14 which receives a striker with which the latch engages. A main actuating lever 16 is operable by an exterior door handle and/or power actuator to release the latch and has an arm 22 carrying a longitudinally slidable drive dog 24. A release lever 18 operable only by an inside door handle is pivoted in a plane normal to the plane of arm 22. A rotatable button 26 in throat 14 so as to be accessible only when the door is open has crank connection to dog 24 to shift it between a drive position at which the levers coact and a disabling position at which movement of release lever 18 will not drive lever 16.

17 Claims, 2 Drawing Sheets

VEHICLE DOOR LATCH MECHANISM

This invention relates to latch mechanism for doors and other closures of vehicles with particular application to the rear passenger doors of cars and light vehicle likely to be accessible to children in the vehicle but remote from immediate adult supervision. It is known to provide the latch mechanism with a child safety facility whereby the latch mechanism can be set to a child safety mode in which the door cannot be unlatched by use of the inside door handle or equivalent inside release facility when the door is shut, the setting means being rendered inaccessible by the closing of the door.

The object of the invention is to provide latch mechanism having a child safety facility which is of particularly simple construction requiring few components, which is economical to manufacture and assemble, and which is reliable and effective in use.

According to the invention there is provided a vehicle door latch mechanism having a child safety facility, and mechanism including a main actuating lever operable by an exterior handle of the door and/or a remotely controlled power actuator in use to release the mechanism for opening the door: an inside release lever operable by an interior handle of the door in use: and a child safety facility having setting means inaccessible when the door is closed for selectively enabling and disabling drive connection of the inside release lever with the main actuating lever: characterised in that said facility includes a drive dog slidingly engaged with an arm of one of said levers for movement longitudinally thereof between a drive position at which it co-acts with an arm of the other of said levers to transmit drive from the inside release lever to the main actuating lever and a disabling position at which it is clear of said arm, and a setting element linked to the dog for effecting said movement and operatively positioned so as to be accessible only when the door is opened.

Conveniently the dog is a slide block carried on an arm of the main actuating lever, and the inside release lever is pivoted for movement in a plane normal to the plane of the latter arm.

The setting element maybe a rotatable button incorporating a crank formation linked to the slide block or other drive dog and indexed for angular movement setting the dog at one or other said position.

Said button or other setting element maybe located on body or base plate of the latch mechanism, e.g. in the mouth of a throat formation of said body or base plate which receives the door post mounted striker with which the latch mechanism engages when the door is closed.

An example of the invention is now more particularly described with reference to the accompanying drawings wherein.

Figure 1:
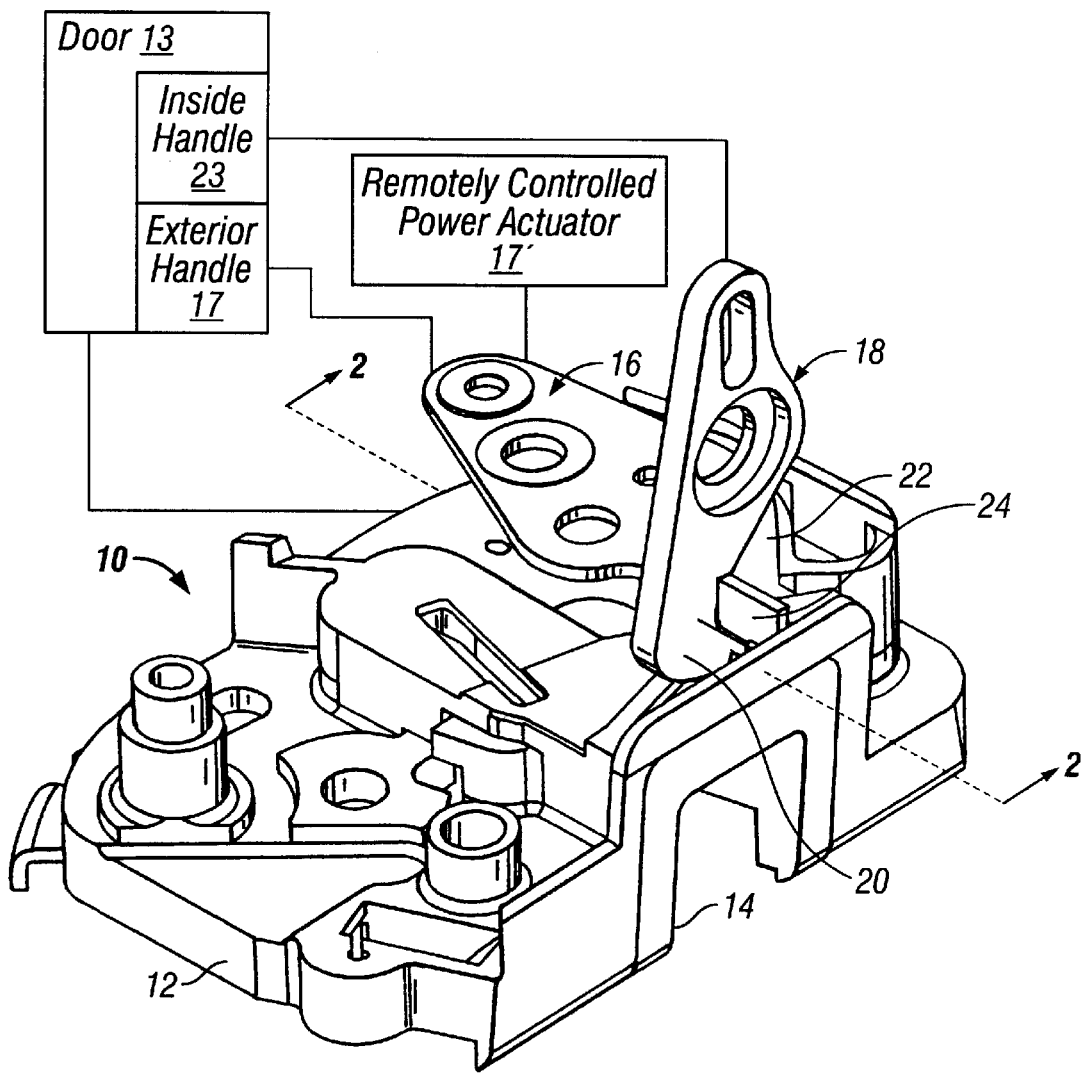
Figure 2:
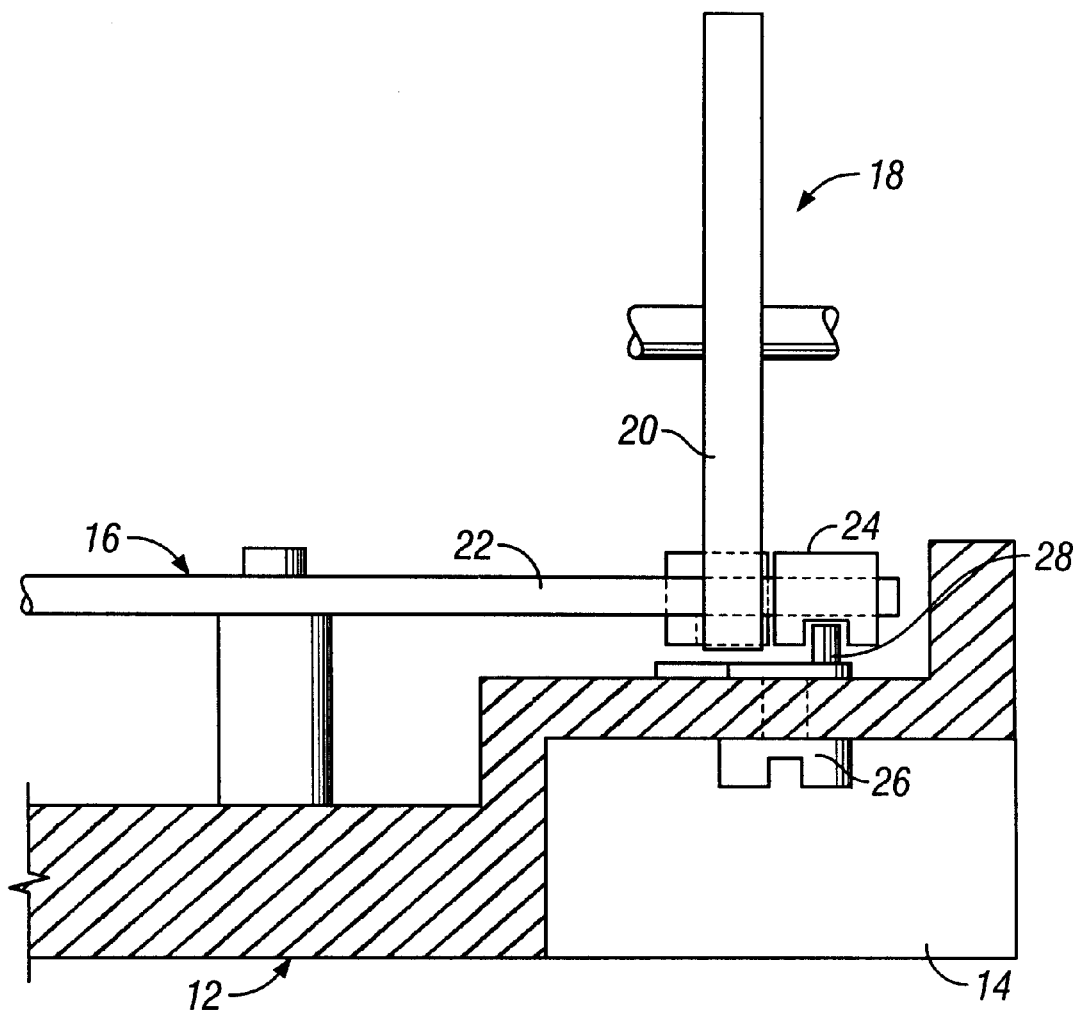

FIG. 1 is a perspective view of a latch mechanism with some parts removed for clarity and, FIG. 2 is a diagrammatic sectional view on line 2—2 of FIG. 1.

The latch mechanism 10 includes a mounting formation base plate 12 to be attached to the respective door 13 in use and defining a throat 14 which receives a door post mounted striker (not shown) engaged by a rotating claw (not shown) which in turn is held by a releasable pawl (not shown) of the latch mechanism to secure the door in known manner.

A main actuating lever 16 is pivoted on the inside of plate 12 in generally parallel relationship to throat 14 and will be linked, in use, to an exterior handle 17 of the door 13, operation of lever 16 disengaged the pawl from the claw so that the door 13 is released for opening. The main actuating lever could also be operated through a remotely controlled power actuator 17'.

An inside release lever 18, fulcrumed on a pivot pin (not shown) carried by a housing portion of the latch body removed for clarity, lies in a vertical plane as viewed in the drawings normal to the plane of movement of lever 16, its lower arm 20 being close to the right hand arm 22 of lever 16. The upper arm of release lever 18 will be operatively linked to an inside handle 23 of the respective door.

A drive dog in the form of a slide block 24 is engaged on lever arm 22 and can be moved longitudinally thereof between a disabling position near the distal end of the arm at which it is clear of the release lever arm 20 and a drive position shown in broken lines in FIG. 2 in which it is in line with the latter arm.

Arm 20 has a hooked end extending towards and below lever arm 22. When block 24 is at the disabling position angular movement of lever 18 is not transmitted to lever 16 as said hooked end merely swings clear below arm 22.

When block 24 is in the drive position it projects below arm 22 in to the path of said hooked end so that lever 18 co-acts with lever 16 and operation of the inside door handle will release the latch mechanism freeing the door for opening.

The child safety facility provided by the above described selective disabling of the drive between the two levers is operated by a setting element in the form of a rotatable button 26 (FIG. 2) journalled through plate 12 and having a slotted head within the mouth of throat 14. The inner end of button 26 carries an eccentric crank pin 28 engaged in a slot in the under face of block 24 shaped so that it does not restrict angular movement of lever 16 but co-acts with the block to move it selectively from one said position to the other by angular movement of button 26. The button can be turned by engaging the end of a key or the like with its stored head, and it is resiliently indexed to urge it positively to the selected position.

It will be seen that button 26 is only accessible when the door is open, thus a parent or other responsible person can set the latch mechanism to child safely condition, ensuring that the door cannot be released by operation of the inside door handle, before shutting the door to contain a child in safety in the rear or other passenger seat of the vehicle.

The child safety facility is particulary simple in construction requiring only a few additional components, is readily assembled as part of unitary latch module for speedy installation into the door on the vehicle assembly line, and is easy to use and reliable and durable in operation.

It will be appreciated that, with some latch mechanism configuration, the slide block or other drive dog could be carried on an arm of the inside release lever for movement between a drive position at which it co-acts with the main actuating lever and a disabling position removing drive connection.

The invention can be embodied in latch mechanisms of all types, whether wholly manually actuated or incorporating remotely controlled power actuation for locking and unlocking and/or powered unlatching.

What is claimed is:

1. Vehicle door latch mechanism including a main actuating lever operable by an exterior handle of the door and/or a remotely controlled power actuator in use to release the mechanism for opening the door, an inside release lever operable by an interior handle of the door in use; and a child safety facility having setting means inaccessible when the door is closed for selectively enabling and disabling drive connection of the inside release lever with the main actuating lever: characterised in that said facility includes a drive dog slidingly engaged with an arm of one of said levers for movement longitudinally thereof between a driven position at which it co-acts with an arm of the other of said levers to transmit drive from the inside release lever to the main actuating lever and a disabling portion at which it is clear of the latter arm, and a setting element linked to the dog for effecting said movement and operatively positioned so as to be accessible only when the door is open, wherein the dog comprises a slide block carried on an arm of the main actuating lever, and the inside release lever is pivoted for movement in a plane normal to the plane of the latter arm.

2. Mechanism as in claim 1 characterised in that the main actuating lever is operable by a remotely controlled power actuator of the mechanism.

3. Mechanism as in claim 1 characterised in that the setting element is a rotatable button incorporating a crank formation linked to the drive dog and indexed for angular movement setting the dog at one or other said position.

4. Mechanism as in claim 3 characterised in that the button is located on a body or base plate, of the latch mechanism.

5. Mechanism as in claim 4 characterised in that the button is located in the mouth of a throat formation of said body or base plate which receives a door post mounted striker with which the latch mechanism engages when the door is closed.

6. Vehicle door latch mechanism including a main actuating lever operable by an exterior handle of the door to release the mechanism for opening the door, an inside release lever operable by an interior handle of the door in use; and a child safety facility that can be selectively set to enable and disable drive connection of the inside release lever with the main actuating lever; said facility comprising a drive dog slidingly engaged with an arm of one of said levers for movement longitudinally thereof between a drive position at which it co-acts with an arm of the other of said levers to transmit drive from the inside release lever to the main actuating lever and a disabling position at which it is clear of the latter arm, and a setting element linked to the dog to effect said movement and operatively positioned so as to be accessible only when the door is open.

7. Mechanism as in claim 6 characterised in that the main actuating lever is operable by a remotely controlled power actuator of the mechanism.

8. Mechanism as in claim 6 wherein the setting element directly engages the dog.

9. Mechanism as in claim 8 characterised in that the main actuating lever is operable by a remotely controlled power actuator of the mechanism.

10. Mechanism as in claim 1 wherein the setting element comprises a rotatable button incorporating a crank formation linked to the drive dog and indexed for angular movement setting the dog at one or other said position.

11. Mechanism as in claim 10 wherein the button is located on a body or base plate of the latch mechanism.

12. Mechanism as in claim 10 characterised in that the main actuating lever is operable by a remotely controlled power actuator of the mechanism.

13. Vehicle door latch mechanism including a main actuating lever operable by a remotely controlled power actuator in use to release the mechanism for operating the door; an inside release lever operable by an interior handle of the door in use; and a child safety facility that can be selectively set to enable and disable drive connection of the inside release lever with the main actuating lever; said facility comprising a drive dog slidingly engaged with an arm of one of said levers for movement longitudinally thereof between a drive position at which it co-acts with an arm of the other of said levers to transmit drive from the inside release lever to the main actuating lever and a disabling position at which it is clear of the latter arm, and a setting element linked to the dog to effect said movement and operatively positioned so as to be accessible only when the door is open.

14. Mechanism as in claim 13 wherein the dog comprises a slide block carried on an arm of the main actuating lever and the inside release lever is pivoted for movement in a plane normal to the plane of the latter arm.

15. Mechanism as in claim 14 characterised in that the setting element is a rotatable button incorporating a crank formation linked to the drive dog and indexed for angular movement setting the dog at one or other said position.

16. Mechanism as in claim 15 characterised in that the button is located on a body or base plate of the latch mechanism.

17. Mechanism as in claim 16 characterised in that the button is located in the mouth of a throat formation of said body or base plate which receives a door post mounted striker with which the latch mechanism engages when the door is closed.

* * * * *